United States Patent [19]
Shinnar et al.

[11] Patent Number: 5,628,906
[45] Date of Patent: May 13, 1997

[54] EXTRACTION PROCESS

[75] Inventors: Reuel Shinnar, Great Neck; Roberto Mauri, New York, both of N.Y.

[73] Assignee: The Research Foundation of the City University of New York, New York, N.Y.

[21] Appl. No.: 274,546

[22] Filed: Jul. 13, 1994

[51] Int. Cl.$^6$ ................................................. B01D 11/04
[52] U.S. Cl. .................................... 210/634; 210/259
[58] Field of Search ................................ 210/634, 511, 210/205, 259

[56] References Cited

U.S. PATENT DOCUMENTS

| | | | |
|---|---|---|---|
| 2,250,976 | 7/1941 | Van Dijck | 23/270.5 |
| 2,361,780 | 10/1944 | Lewis | 196/13 |
| 3,427,357 | 2/1969 | de Gramont et al. | 260/652 |
| 3,898,291 | 8/1975 | Darsi et al. | 260/643 D |
| 3,936,489 | 2/1976 | Rozsa et al. | 260/463 |
| 4,261,818 | 4/1981 | Sweeney | 210/511 |
| 4,336,106 | 6/1982 | Winter, III | 196/14.52 |
| 4,493,765 | 1/1985 | Long et al. | 208/45 |
| 4,632,809 | 12/1986 | Otto et al. | 422/254 |
| 4,732,685 | 3/1988 | Brandt et al. | 210/634 |
| 4,770,780 | 9/1988 | Moses | 210/634 |
| 4,863,607 | 9/1989 | Andrew et al. | 210/634 |
| 4,877,530 | 10/1989 | Moses | 210/511 |
| 4,954,260 | 9/1990 | Ludmer et al. | 210/634 |
| 5,049,279 | 9/1991 | Bitar et al. | 210/634 |
| 5,078,886 | 1/1992 | Hsu | 210/632 |
| 5,244,575 | 9/1993 | Marshall | 210/634 |
| 5,282,974 | 2/1994 | Hart | 210/639 |

OTHER PUBLICATIONS

P. A. Schweitzer, ed., *Handbook of Separation Techniques for Chemical Engineers*, New York: McGraw Hill, selected pages.

R. Blumberg, *Liquid–Liquid Extraction*, London: Academic Press (1988), pp. 43–44, 52–54.

Z. Ludmer et al., "Solubility in Binary Mixtures at the Immiscibility Critical Point," *AIChE Journal*, 33:11 (Nov. 1987), pp. 1776–1780.

A. Ullmann et al., "Novel Separation Process Using Solvents with a Critical Point of Miscibility," *Proc. A.I.Ch.E. Conference*, Miami, Florida (1993).

A. Veide et al., "A Process for Large–Scale Isolation of β–Galactosidase from *E. Coli* in an Aqueous Two–Phase System," *Biotechnolgy and Bioengineering*, vol. XXV (1983), pp. 1789–1800.

T. P. Castor et al., "Determination of Taxol in *Taxus Media* Needles in the Presence of Interfering Components," *Journal of Liquid Chromatography*, 16(3), 723–731 (1993).

Matkovich et al. Salting–out Acetone from Water–Basis of a New Solvent Extraction System, from Anal. Chem., vol. 45, No. 11, 9–1973, pp. 1915–1921.

*Primary Examiner*—Frank Spear
*Attorney, Agent, or Firm*—Darby & Darby

[57] ABSTRACT

The invention relates to an extraction process which comprises adding a primary solvent to a first solution containing a solute dissolved in a native solvent. The primary solvent is added in an amount sufficient to form a single-phase mixture comprising said primary solvent, said native solvent and said solute. Thereafter a modifier is added to the single-phase solution. The modifier is miscible with either the primary solvent or the native solvent and serves to reduce the miscibility of the primary solvent with the native solvent so as to form a two-phase mixture. The two phases are allowed to separate into one phase rich in the native solvent and a second phase rich in the primary solvent and solute. Finally, the solute is separated from the solvent-rich phase. The process is particularly useful for separating products of fermentation from fermentation broths or other systems which are sensitive to high temperatures or which tend to form emulsions.

15 Claims, 1 Drawing Sheet

EXTRACTION PROCESS

BACKGROUND OF THE INVENTION

Liquid-liquid extraction (LLE) is a crucial step in the manufacturing of a wide range of products. Such processes are used for the extraction of one compound and as well as for separation between two or more compounds (fractional extraction).

The LLE process is simple in concept and usually requires the contacting of a feed containing the solute to be extracted with a solvent. This solvent/feed mixture is usually immiscible, but may be partially miscible.

The extraction and the stripping involve liquid-liquid contacting in which the droplets of one phase are initially dispersed in a second phase to facilitate mass transfer across the liquid-liquid boundary. Basically, there are two types of LLE units, those in which each individual stage is a separate unit termed "mixer settlers" and those in which several stages are integrated into one column. Multi-stage columns can be simple spray or packed columns, or can have stages equipped with various types of mixing devices separated by coalescence sections. The stage efficiency and the throughput of such devices are, obviously, directly related to the mass transfer and the coalescence rates.

To form small drops and ensure good contact between the phases, in slow mass-transfer systems, high intensity mixing is required. However, the shear stress induced by such a mixing can, in many cases, damage high molecular weight molecules. In addition, the intense mixing forms fine dispersions which reduce the coalescence rate or, in the presence of surface active impurities, may even cause a "stable emulsion", one of the operating hazards of solvent extraction equipment.

From the point of view of LLE processes, the stability of the dispersion is its most important property, since the phases must separate at each extraction stage. For all practical purposes, the breakup time or the coalescence rate will determine the workable throughput of the extraction equipment. In countercurrent column-type contactors, steady operation is possible only when the rate of droplets arrival does not exceed the coalescence rate at the main interface; otherwise the dispersed band will extend over the entire column, leading to flooding. In mixer-settler contactors, the dimensions of the settler are designed according to the coalescence rate, and increasing the throughput above the coalescence rate will result in flooding of the settler. It is clear, therefore, that systems with emulsification tendencies cannot be operated by conventional extractors. Commonly such systems are handled in centrifugal extractors or by filtration. In some cases, adding compounds that break the emulsion can minimize the problem. This, however, makes complex the final purification of the product.

Emulsion formation is a common problem in the pharmaceutical industry, where the desired products are frequently extracted from the fermentation broth by organic solvents and in extraction processes where mechanical agitation is used to increase the mass transfer rates.

U.S. Pat. No. 4,954,260 of Z. Ludmer, R. Shinnar, and V. Yakhot ("the U.S. Pat. No. '260 patent") describes a process that overcomes some of these difficulties. In that case, special solvents are used that at one temperature form a homogeneous, one-phase mixture and, at a higher or lower temperature, form two phases, one solvent-rich and the other water-rich. See, also, Ullmann, Ludmer and Shinnar, "Novel Separation Process Using Solvents with a Critical Point of Miscibility," *Proc. A.I.Ch.E. Conference*, Miami, Fla. (1993).

The process is composed of two stages, the heating Stage and the cooling stage where the mixture is cooled across the coexistence curve. Only very mild agitation is required. Compared to the mixing stage of the conventional isothermal extraction process, the heating stage provides a greatly improved contacting area, since in such stage there is but a single phase. Even more importantly, in the process of the U.S. Pat. No. '260 patent, the cooling stage has great advantage over the settling stage of the conventional extraction process: namely, when the cooling is fast enough, rapid phase-separation occurs even in the presence of impurities and cell debris. Accordingly, the need to use centrifuges is eliminated.

Unfortunately, as a practical matter the process has the disadvantage of requiring continual and rapid heating and cooling.

BRIEF DESCRIPTION OF THE INVENTION

In accordance with the invention, it has now been discovered that an extraction process can be conducted by first mixing the system to be extracted with a primary solvent, which is soluble with the native solvent, and subsequently adding a modifier, which is insoluble with either the native or the primary solvent. By adding the modifier, the solubility of the primary solvent with the native solvent is changed, thereby causing a near instantaneous phase separation. The solute to be extracted will be concentrated in the primary-solvent-rich phase. The technique of the invention can be applied to both single- and multi-stage processes.

The inherent advantage of this method is that it works effectively even in the presence of substances (solid or dispersed) that cause the formation of emulsions or stable dispersions. Though the effect of adding a modifier on the solubility of a solvent mixture is known, that such addition can result in rapid phase separation, even in the presence of emulsion-forming impurities, had not heretofore been observed in connection with an extraction process. In addition, this new process leads to improved recovery of the solute to be extracted, especially when there are barriers to the extraction, such as cell boundaries. This is because the primary solvent, being soluble with the native solvent, can easily penetrate the system to be extracted, thereby increasing the yield of the process.

The technique of the invention can be applied to both single- and multi-stage processes. While the effect of adding the secondary solvent or modifier on the solubility of a solvent mixture is known, that such addition can result in rapid phase separation, even in the presence of emulsion-forming impurities, had not heretofore been appreciated in an extraction process.

The method of the invention results in equipment savings, lower product degradation and improved extraction yield. Moreover, it has the following unanticipated, but very significant advantages over the prior art processes.

a) The final compositions of the water-rich and solvent-rich phases can be adjusted over a wider range to achieve the desired separation. There is no concern that high temperatures may be required to reach the single-phase region.

b) There is no need for separate heat transfer equipments, as the extraction can be carried out in the single vessel, e.g., a fermentation vessel. Alternatively, low cost settlers may be used for large volume production.

c) The difficulty of rapidly cooling large amounts of liquid is eliminated. Re-emulsification during cooling does not occur.

d) The range of primary and secondary solvents that can be used is much greater due to the elimination of the temperature constraint.

BRIEF DESCRIPTION OF THE FIGURE

The figure is a three-component diagram illustrating the process of Example 1.

DETAILED DESCRIPTION OF THE INVENTION

Figure 1:
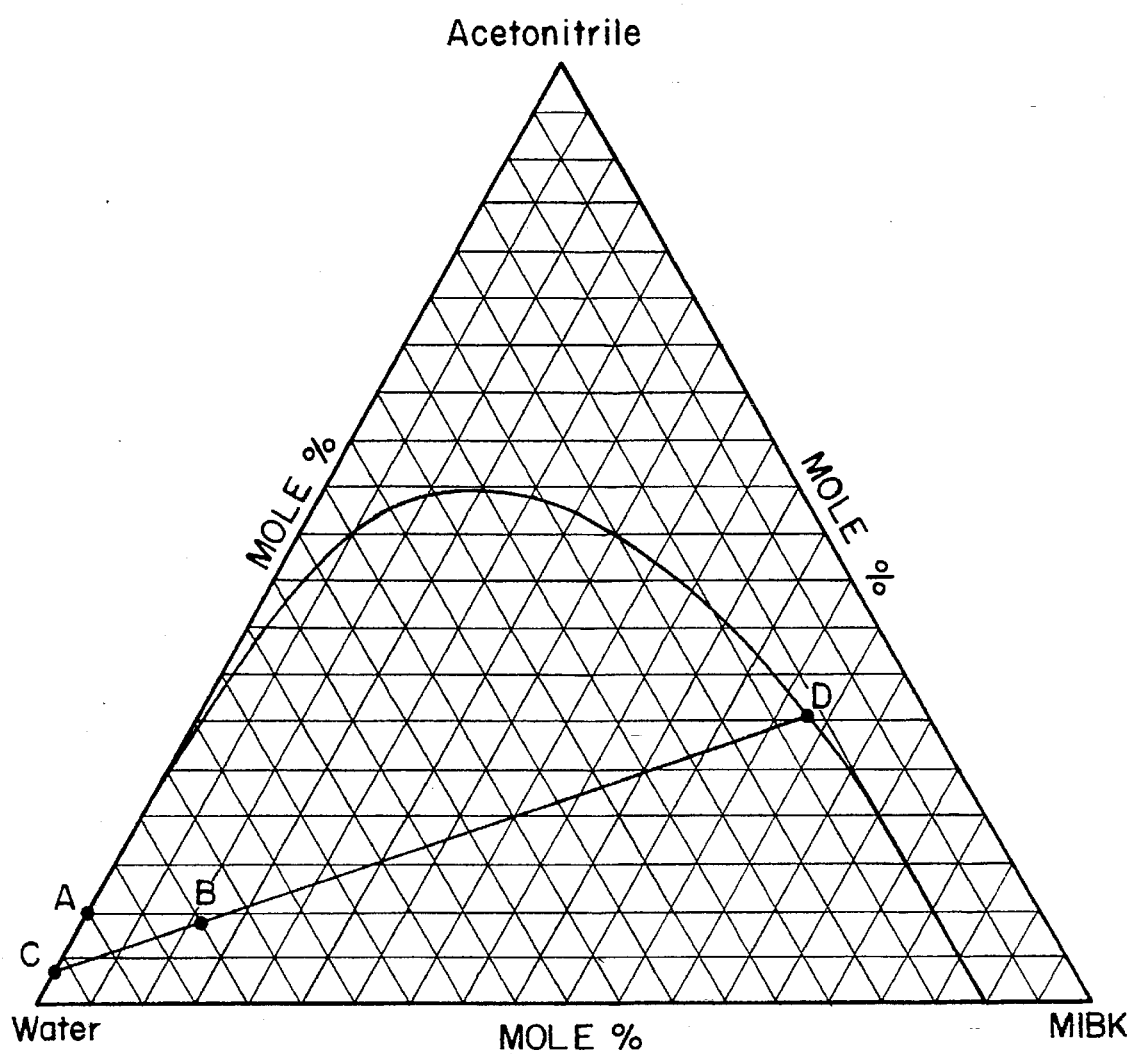

In the first step, a primary solvent is added to the system to be extracted. This system comprises a solution containing the solute to be extracted dissolved in a native solvent, e.g., water. It can be any complex solution or dispersion containing a material soluble in the primary solvent. The primary solvent is completely miscible with the system to be extracted at the processing temperature (most generally room temperature).

Secondly, a second solvent or modifier is added to the mixture from step 1. The modifier serves to reduce the miscibility of the primary solvent with the material being extracted, e.g., water, so that at the given temperature two separate phases will form, one water-rich and the other solvent-rich, which will be referred to herein as raffinate and extract, respectively. By following this procedure, the solute to be extracted is contained mainly in the primary solvent-rich phase, i.e., the extract. The effect of this step can be achieved by using as a modifier either a compound that is much more soluble in the primary solvent than in the native solvent or, vice versa, a compound that is much more miscible with the native solvent than with the primary solvent. Thus, for the acetonitrile/water mixture, the addition of sodium chloride (which is miscible with water and immiscible with acetonitrile) causes a separation which is at least as rapid as that achieved by adding toluene or methyl isobutyl ketone (which are miscible with acetonitrile and immiscible with water).

Thirdly, the two phases are allowed to separate. This occurs very rapidly, within less than one minute, and without the need of a centrifuge. In particular, the emulsion-forming materials, such as the cell fragments of a fermentation broth, remain in the raffinate, while the top, solvent-rich phase is clear. This facilitates the successive extraction of the solute, which can be carried over via a standard crystallization process.

The small amount of the primary and secondary solvent in the water-rich phase is easily removed by distillation. The solute of interest can be extracted from the primary solvent-rich phase by standard methods.

Applications where the process of the invention may bring about significant advantages include:

1) The extraction of a fermentation broth both in a batch or a continuous process. This avoids the need to centrifuge and gives better yields due to better contact during the mixing stage.

2) The extraction of different compounds from natural plant or animal materials. Due to the presence of a single water-rich phase, improved contacting between the solvent and the material to be extracted is achieved. Here there is no water-solvent interface and no wetting problems, and the solvent can easily penetrate the cell walls, thereby increasing the yield of the process.

3) The extraction of fermentation products continuously during fermentation. Here, part of the broth is removed from the fermentator, extracted as discussed above, and returned to the fermentator. This is useful where the product inhibits further reactions, as for example in the production of ethyl alcohol from sugar. Conventional process requires centrifugation, which is harmful to the organisms.

4) Replacement of solvents which are environmentally objectionable, e.g., extractions processes using chlorinated solvents. The process of the invention is not only more powerful and versatile, but also permits the use of solvents which are environment-friendly.

While the above describes single-stage extractions, multi-stage extractions are also feasible, although, because of the efficiency of the process, they are seldom required for the cases described here.

Other systems which may advantageously be extracted in accordance with the teachings of the invention include: a) extraction of alkaloids and other substances from plant materials; b) extraction of intracellular proteins and enzymes from microorganisms; c) removal of chemical hazardous products from industrial waste water; d) extraction of chemical compounds, such as ethanol, from the water solutions obtained from the fermentation of corn or other vegetable products. This list is not intended to be exhaustive, as many other applications will be obvious to a practitioner.

One skilled in the art can readily determine the appropriate solvents and modifiers that are useful in connection with the invention. Generally speaking, the primary solvent is an organic compound that is miscible with the system to be extracted. In particular, if the native solute is water, examples of primary solvents are: acetaldehyde, acetic acid, acetonitrile, butanoic acid, ethanol, formic acid, methanol, propanoic acid, 1-propanol, 2-propanol, 2-propanone (acetone), propenoic acid, and pyridine. Additional examples of primary solvents of this kind are listed in Table I:

TABLE I

Examples of Primary Solvents Compatible With Water-Based Systems to be Extracted

| | |
|---|---|
| acetaldehyde | $CH_3CHO$ |
| acetic acid | $CH_3CO_2H$ |
| acetic acid, amide, N,N-dimethyl | $C_4H_9NO$ |
| acetic acid, dichloro | $C_2H_2Cl_2O_2$ |
| acetic acid, nitrile (acetonitrile) | $CH_3CN$ |
| amine, diethyl | $C_4H_{11}N$ |
| amine, diethyl, 2,2'-dihydrxy | $C_4H_{11}NO_2$ |
| amine, triethyl, 2,2',2"-trihydroxy | $C_6H_{15}NO_3$ |
| butane, 1-amino | $C_4H_{11}N$ |
| 2,3-butanediol (meso) | $C_4H_{10}O_2$ |
| 1,3-butanediol, 3-methyl | $C_5H_{12}O_2$ |
| butanoic acid | $C_4H_8O_2$ |
| cycloheptane, 1-aza | $C_6H_{13}N$ |
| 1,4-dioxane | $C_4H_8O_2$ |
| 1,2-ethanediol | $C_2H_6O_2$ |
| ethanol | $C_2H_6O$ |
| ethanol, 2-amino | $C_2H_7NO$ |
| ethanol, 2-butoxy | $C_6H_{14}O_2$ |
| ethanol, 2-chloro | $C_2H_5ClO$ |
| ethanol, 2-ethoxy | $C_4H_{10}O_2$ |
| formic acid | $CH_2O_2$ |
| formic acid, amide | $CH_3NO$ |
| formic acid, amide, N-methyl | $C_2H_5NO$ |
| formic acid, amide, N,N-dimethyl | $C_3H_7NO$ |
| furan, tetrahydro | $C_4H_8O$ |
| hexanoic acid, 6-amino, lactam | $C_6H_{11}NO$ |
| methanol | $CH_4O$ |
| morpholine | $C_4H_9NO$ |
| nicotine | $C_{10}H_{14}N_2$ |
| 2-pentanone, 4-hydroxy, 4-methyl | $C_6H_{12}O_2$ |
| piperidine | $C_5H_{11}N$ |
| 1,2,3-propanetricarboxylic acid | $C_6H_8O_6$ |
| propanoic acid | $C_3H_6O_2$ |
| propanoic acid, 2-hydroxy | $C_3H_6O_3$ |
| propanoic acid, 3-hydroxy, nitrile | $C_3H_5NO$ |
| 1-propanol | $C_3H_8O$ |
| 2-propanol | $C_3H_8O$ |

TABLE I-continued

Examples of Primary Solvents Compatible
With Water-Based Systems to be Extracted

| | |
|---|---|
| 2-propanol, 1,3-bis (dimethylamino) | $C_7H_{18}N_2O$ |
| 2-propanol, 2-methyl | $C_4H_{10}O$ |
| 2-propanone (acetone) | $C_3H_6O$ |
| propenoic acid | $C_3H_4O_2$ |
| propenoic acid, 2-methyl, amide | $C_4H_7NO$ |
| pyridine | $C_5H_5N$ |
| pyridine, 2-methyl | $C_6H_7N$ |
| 2-pyrrolidone, 1-methyl | $C_5H_9NO$ |
| succinic acid | $C_4H_6O_4$ |
| sulfone, tetramethylene | $C_4H_8O_2S$ |
| triethylene glycol, dimethyl ether | $C_8H_{18}O_4$ |

As noted above, the secondary solvents or modifiers serve to increase the solubility of the primary solvent in the native solvent, the latter in most instances being water. This is achieved by choosing as modifier a compound that is either immiscible with the native solvent and miscible with the primary solvent (modifier of the first kind) or, vice versa, miscible with the native solvent and immiscible with the primary solvent (modifier of the second kind).

In particular, if the native solvent is water and the primary solvent is one of the organic compounds listed in Table I, examples of modifiers of the first kind are: acetic acid, 3-methylbutyl ester; acetic acid, pentyl ester; benzene; benzene, chloro; benzene, isopropyl; benzene, nitro; butanoic acid, ethyl ester; butanoic acid, methyl ester; cyclohexane; ethane, 1,2-dichloro; ethane, 1,1,2-trichloro; ethene; tetrachloro; ethene, trichloro; ether, dibutyl; ether, diphenyl; fenchone; 1-heptadecanol; heptane; hexane; methane, dichloro; methane, tetrachloro; pentane; 2-pentanone, methyl isobutyl ketone (MIBK); tetralin; toluene. Additional examples of modifiers of the first kind are listed in Table II.

TABLE II

Examples of Modifiers of the First Kind
to be Used With a Water-Based System to be
Extracted With One of the Primary Solvents of Table I

| | |
|---|---|
| acetaldehyde, diacetate | $C_6H_{10}O_4$ |
| acetic acid, butyl ester | $C_6H_{12}O_2$ |
| acetic acid, cyclohexyl ester | $C_8H_{14}O_2$ |
| acetic acid, ethenyl ester | $C_4H_6O_2$ |
| acetic acid, ethyl ester | $C_4H_8O_2$ |
| acetic acid, isobutyl ester | $C_6H_{12}O_2$ |
| acetic acid, isopropyl ester | $C_5H_{10}O_2$ |
| acetic acid, methyl ester | $C_3H_6O_2$ |
| acetic acid, 3-methylbutyl ester | $C_7H_{14}O_2$ |
| acetic acid, octyl ester | $C_{10}H_{20}O_2$ |
| acetic acid, pentyl ester | $C_7H_{14}O_2$ |
| acetic acid, propyl ester | $C_5H_{10}O_2$ |
| amine triethyl | $C_6H_{15}N$ |
| aniline | $C_6H_7N$ |
| aniline N,N-dimethyl | $C_8H_{11}N$ |
| benzaldehyde | $C_7H_6O$ |
| benzene | $C_6H_6$ |
| benzene, bromo | $C_6H_5Br$ |
| benzene, chloro | $C_6H_5Cl$ |
| benzene, 1,2-dimethyl | $C_8H_{10}$ |
| benzene, 1,3-dimethyl | $C_8H_{10}$ |
| benzene, 1,4-dimethyl | $C_8H_{10}$ |
| benzene, ethyl | $C_8H_{10}$ |
| benzene, isopropyl | $C_9H_{12}$ |
| benzene, nitro | $C_6H_5NO_2$ |
| benzoic acid, ethyl ester | $C_9H_{10}O_2$ |
| 1,3-butadiene, 2,3-dichloro | $C_4H_4Cl_2$ |
| butanoic acid, 2-ethyl | $C_6H_{12}O_2$ |
| butanoic acid, ethyl ester | $C_6H_{12}O_2$ |

TABLE II-continued

Examples of Modifiers of the First Kind
to be Used With a Water-Based System to be
Extracted With One of the Primary Solvents of Table I

| | |
|---|---|
| butanoic acid, methyl ester | $C_5H_{10}O_2$ |
| butanoic acid, 3-methyl, ethyl ester | $C_7H_{14}O_2$ |
| 1-butanol | $C_4H_{10}O$ |
| 2-butanol | $C_4H_{10}O$ |
| 1-butanol, 3-methyl | $C_5H_{12}O$ |
| 2-butanone | $C_4H_8O$ |
| 3-buten-2-one | $C_4H_6O$ |
| cyclohexane | $C_6H_{12}$ |
| cyclohexane, methyl | $C_7H_{14}$ |
| cyclohexanol | $C_6H_{12}O$ |
| cyclohexanone | $C_6H_{10}O$ |
| cyclohexene | $C_6H_{10}$ |
| decane | $C_{10}H_{22}$ |
| 1,3-dioxane, 4,4-dimethyl | $C_6H_{12}O_2$ |
| ethane, 1,1-dichloro | $C_2H_4Cl_2$ |
| ethane, 1,2-dichloro | $C_2H_4Cl_2$ |
| ethane, nitro | $C_2H_5NO_2$ |
| ethane, 1,1,2-trichloro | $C_2H_3Cl_3$ |
| ethene, tetrachloro | $C_2Cl_4$ |
| ethene, trichloro | $C_2HCl_3$ |
| ether, dibutyl | $C_8H_{18}O$ |
| ether, diethyl | $C_4H_{10}O$ |
| ether, diisopropyl | $C_6H_{14}O$ |
| ether, diphenyl | $C_{12}H_{10}O$ |
| fenchone | $C_{10}H_{16}O$ |
| formic acid, ethyl ester | $C_3H_6O_2$ |
| furfural | $C_5H_4O_2$ |
| 1-heptadecanol | $C_{17}H_{36}O$ |
| heptane | $C_7H_{16}$ |
| 1-heptanol | $C_7H_{16}O$ |
| 4-heptanone | $C_7H_{14}O$ |
| 4-heptanone, 2,6-dimethyl | $C_9H_{18}O$ |
| hexane | $C_6H_{14}$ |
| hexanoic acid | $C_6H_{12}O_2$ |
| hexanoic acid, 2-ethyl | $C_8H_{16}O_2$ |
| 1-hexanol | $C_6H_{14}O$ |
| 1-hexanol, 2-ethyl | $C_8H_{18}O$ |
| 1-hexene | $C_6H_{12}$ |
| isophorone | $C_9H_{14}O$ |
| methane, dichloro | $CH_2Cl_2$ |
| methane, nitro | $CH_3NO_2$ |
| methane, tetrachloro | $CCl_4$ |
| methane, trichloro | $CHCl_3$ |
| naphtalene, 1-methyl | $C_{11}H_{10}$ |
| nonane | $C_9H_{20}$ |
| 1-nonanol | $C_9H_{20}O$ |
| octane | $C_8H_{18}$ |
| 1-octanol | $C_8H_{18}O$ |
| 1-octene | $C_8H_{16}$ |
| pentane | $C_5H_{12}$ |
| pentane, 2,2,4-trimethyl | $C_8H_{18}$ |
| pentanoic acid, ethyl ester | $C_9H_{18}O_2$ |
| 1-pentanol | $C_5H_{12}O$ |
| 2-pentanol, 4-methyl | $C_6H_{14}O$ |
| 3-pentanone | $C_5H_{10}O$ |
| 2-pentanone, 4-methyl (MIBK) | $C_6H_{12}O$ |
| propane, 1-nitro | $C_3H_7NO_2$ |
| propanoic acid, ethyl ester | $C_5H_{10}O_2$ |
| propanoic acid, methyl ester | $C_4H_8O_2$ |
| propanoic acid, propyl ester | $C_6H_{12}O_2$ |
| propenoic acid, 2-methyl, methyl ester | $C_5H_8O_2$ |
| propenoic acid, nitrile | $C_3H_3N$ |
| styrene | $C_8H_8$ |
| toluene | $C_7H_8$ |
| toluene, 2-chloro | $C_7H_7Cl$ |
| toluene, 3-chloro | $C_7H_7Cl$ |
| toluene, 4-chloro | $C_7H_7Cl$ |

Examples of modifiers of the second kind, that are miscible with water and immiscible with most of the primary solvents of Table I, are most of the electrolytes, such as sodium chloride, potassium chloride, sodium hydroxide, chloric acid, and silver nitrate. Additional examples of modifiers of the second kind are listed in Table III.

TABLE III

Examples of Modifiers of the Second Kind
to be Used With a Water-Based System to be
Extracted With One of the Primary Solvents of Table I

| | |
|---|---|
| Ammonium chloride | $NH_4Cl$ |
| Barium Chloride | $BaCl_2$ |
| Calcium Chloride | $CaCl_2$ |
| Calcium hydroxide | $Ca(OH)_2$ |
| Chloric acid | $HCl$ |
| Copper sulfate | $Cu_2SO_4$ |
| Lanthanum chloride | $LaCl_3$ |
| Lithium chloride | $LiCl$ |
| Lithium per-chlorate | $LiClO_4$ |
| Magnesium chloride | $MgCl_2$ |
| Potassium bromide | $KBr$ |
| Potassium chloride | $KCl$ |
| Potassium hydrogen carbonate | $KHCO_3$ |
| Potassium hydroxide | $KOH$ |
| Potassium iodide | $KI$ |
| Potassium meta-periodate | $KIO_4$ |
| Potassium nitrate | $KNO_3$ |
| Potassium per-chlorate | $KClO_4$ |
| Potassium per-manganate | $KMnO_4$ |
| Potassium phosphate | $K_2HPO_4$ |
| Potassium per-rhenate | $KReO_4$ |
| Silver nitrate | $AgNO_3$ |
| Sodium chloride | $NaCl$ |
| Sodium hydroxide | $NaOH$ |
| Sodium iodide | $NaI$ |
| Sodium per-chlorate | $NaClO_4$ |
| Sodium sulfate | $Na_2SO_4$ |
| Strontium chloride | $SrCl_2$ |
| Zinc sulfate | $ZnSO_4$ |

As noted above, among the advantages of the invention is that the entire process may be carried out at substantially the same temperature, most economically at room temperature. In certain circumstances temperatures other than room temperature may be advantageously employed to facilitate the separation. For example, when the system to be separated is water-based, the amount of primary solvent contained in the raffinate decreases at lower temperatures, thereby increasing the efficiency of the separation process and concomitantly simplifying the task of extracting the solvents from the raffinate. Thus, whenever the solute to be extracted is very valuable and/or the primary solvent or the modifier is toxic, it may be economically advantageous to carry out the separation process at temperatures lower than ambient. Another reason for using lower temperatures is to minimize any undesirable interactions between the compound to be extracted and the solvents. On the other hand, higher temperatures are sometimes desirable to improve solubility.

The process is advantageously carried out at atmospheric pressure, though higher and lower pressures may be used in certain instances. For example, if the modifier is a very volatile compound, the separation should be carried out at a pressure sufficiently high so that the system is in the liquid state. The advantage of this technique is that the volatile solvent can be subsequently extracted by simply bringing the pressure of the system back to ambient conditions. In general, higher pressures are needed to control the volatility of the primary solvent and the modifier. This not only allows the use of higher temperatures, thereby increasing the solubilities, but also extends the choice of primary solvents and modifiers to compounds that otherwise could not be used. In addition, solvents and modifiers could be partially recovered by changing the pressure.

One skilled in the art may readily select the amount of solvents and modifiers which may be used. Generally speaking, sufficient primary solvent must be used to substantially completely dissolve the initial solution to be extracted. This can be readily determined by experimentation. There would be no particular advantage in using larger amounts of solvent; however, some excess may facilitate forming the solution. Of course, the primary solvent must be one in which the solute is at least moderately soluble.

The amount of secondary solvent or modifier must be sufficient to reduce the solubility of the native solvent in the primary solvent so that two phases are formed.

The optimum amount of modifier that is added is determined by balancing the extraction of excess solvent from the raffinate or from the extract against the economic gain derived from the higher amount of solute recovered in the extract.

Conventionally, upon the addition of the secondary solvent or modifier, gentle stirring is employed to facilitate contact between the components. After the mixing, as noted above, the settling of the two phases is rapid. Often this occurs substantially instantaneously, generally in less than one minute. Since only gentle mixing is employed, there is little tendency for the materials to emulsify and the phases may be completely separated.

Where a secondary solvent is employed, this solvent (along with the primary solvent and the solute) is found in the solvent-rich phase. Alternatively, where a modifier such as salt is employed, the solvent-rich phase would contain predominantly the primary solvent and the solute, while the native solvent phase may contain dissolved therein the modifier.

After the two phases are separated, the solute is separated from the solvent-rich phase by conventional means (e.g., distillation). Where the solute is temperature-sensitive, vacuum distillation or evaporation may be beneficially used.

EXAMPLE 1

As an example of the invention, the extraction of efrotomycin from a fungal fermentation broth containing about 5 grams per liter of efrotomycin and 6% (dry weight) of disintegrated actinomycete cells was performed. This fermentation broth, 100 cc, was mixed with 33 cc of acetonitrile (ACN) at room temperature 25° C. to obtain a homogeneous mixture, since, at any temperature above 0° C., this amount of ACN is completely miscible with water. After letting the mixture settle for 2 minutes, 118 cc of MIBK was added, thus causing the homogeneous mixture to separate immediately into 132 cc of a water-rich phase (raffinate) and 119 cc of a solvent-rich phase (extract). At the end of the separation, all the cell fragments were confined to the water-rich phase. The extract was clear, with no visible trace of impurities. After 1 minute, a sample of the upper, solvent-rich phase was removed and its composition analyzed. The total amount of efrotomycin extracted was about 95% of the initial amount.

In a comparative experiment, efrotomycin was extracted using a conventional process, where MIBK was used as solvent with a 1.5:1 ratio of MIBK to water. A centrifuge had to be used to separate the two phases. In this case, only about 75% of the initial amount of efrotomycin was extracted, that is, about 20% less than the amount extracted using the process of the invention.

This process is diagrammatically illustrated in the Figure, where the molar compositions are indicated in a triangular diagram. Here points A (90% water, 10% ACN) and B (78% water, 8.7% ACN, 13.3% MIBK) describe the system in the mixing stage and after the addition of MIBK, respectively. Points C (95.9% water, 3.9% ACN, 0.2% MIBK) and D (11.7% water, 30.8% ACN, 57.5% MIBK) describe the water-rich and the solvent-rich phases, respectively.

Similar results were obtained by using different initial compositions of water, acetonitrile, and MIBK, by replacing the acetonitrile with acetone or butanol, and by using toluene or salt instead of MIBK.

In the first step, conventionally, this process is carried out by mixing the broth with a solvent mixture, such as MIBK, which is essentially immiscible or has a low solubility with water, and then separating the solvent. Since isothermal mixing forms a stable emulsion that will not separate even after 30 hours, this separation requires the use of a centrifuge.

Alternatively, the extraction of efrotomycin can be achieved by using the process described in the U.S. Pat. No. '260 patent where a mixture composed of the broth together with an acetonitrile/MIBK solvent is first heated to a temperature above 40° C. to form a single phase, and then cooled down to 25° C., where within one minute it separates into two phases. The composition range of the solvent is limited because the temperature of the single-phase region must be low enough to prevent degradation.

On the other hand, using the extraction process of the invention, the same rapid separation can be achieved isothermally, by first mixing acetonitrile and the broth and then adding MIBK to cause their separation. In this case, the operating temperature can be chosen at will and the relative amount of acetonitrile and MIBK can be adjusted over a very wide range.

EXAMPLE 2

Here, the experiment of Example 1 was repeated using different amounts of ACN and MIBK. Specifically, the fungal fermentation broth described above, 100 cc, was mixed with 78 cc of ACN. Subsequently, 46 cc of MIBK were added. A water-rich phase, 129 cc, with a 89.2% water/10.4% ACN/0.4% MIBK molar composition and 95 cc of a solvent-rich phase with a 27.0% water/53.6% ACN/19.4% MIBK molar composition were obtained. At the end of the separation, the top, solvent-rich phase was clear, with no visible sign of cell fragment. It contained about 75% of the initial amount of efrotomycin.

EXAMPLE 3

In another experiment, the intracellular enzyme beta-galactosidase was extracted from an aqueous suspension containing 3% dry weight of disintegrated *E. coli* cells at a temperature of 20° C. The aqueous suspension, 100 cc, was mixed with 10 cc of polyethylene glycol (PEG) and then 10 grams of potassium phosphate (PP). A water-rich phase, 90 cc, with an 87% water/1% PEG/12% PP weight composition and 30 cc of a solvent-rich phase with a 78% water/16% PEG/6% PP weight composition were obtained. At the end of the separation the top, solvent-rich phase was clear, with no visible cell fragment, and contained about 95% of the original amount of the galactosidase enzyme.

A similar extraction process was described by Veirde, Smeds and Enfors in *Biotechnology and Bioengineering*, Volume 25, page 1789 (1983), who used an aqueous, two-phase system composed of polyethylene glycol (PEG) and a salt for recovering the enzyme. In their process, Veirde et al. added PEG and a salt at the same time, and then separated the two phases using a centrifuge.

EXAMPLE 4

In yet another experiment, taxol, a potent anticancer agent, was extracted at a temperature of 20° C. from the ground needles of the taxus brevifolia tree. To 120 cc of an aqueous suspension containing about 20% dry weight of ground needles was mixed 100 cc of acetonitrile. Thereafter, 20 grams of sodium chloride were added. A water-rich phase, 156 cc, containing all the ground needles, with a 84.4% water/10.2% ACN/5.4% salt molar composition and a solvent-rich phase, 77 cc, with a 19.6% water/80.4% ACN/0% salt molar composition and containing 99% of the taxol originally present in the suspension were formed.

EXAMPLE 5

A fermentation broth, 100 cc, is mixed with 134 cc of acetone. Subsequently, 41 cc of toluene are added. A water-rich phase, 184 cc, with a 82.6% water/17.2% acetone/0.2% toluene molar composition and 91 cc of a solvent-rich phase with a 13.8% water/58.9% acetone/27.3% toluene molar composition are obtained.

EXAMPLE 6

A fermentation broth, 100 cc, is mixed with 101 cc of ACN and then 24 cc of toluene are added. A water-rich phase, 125 cc, with a 86.7% water/13.1% ACN/0.2% toluene molar composition and 100 cc of a solvent-rich phase with a 13.6% water/66.9% ACN/19.5% toluene molar composition are obtained.

In Examples 5 and 6, as soon as the modifier is added, a complete separation of the two phases (raffinate and extract) is achieved within less than one minute, despite the presence of cell debris and other surface-active materials in the fermentation broth. The efficiency of the recovery of the solute, being a function of the amount of primary solvent present in the raffinate, will be different in each example. By properly choosing the primary solvent and the modifier, the total amount of solute extracted can be considerably higher than that obtained with a conventional extraction, with the obvious advantage that no centrifuge is required when using the method of the invention. The solute can thereafter be separated from the solvent via a standard crystallization process.

What is claimed is:

1. A liquid-liquid extraction process wherein a solute is transferred at a high mass transfer rate from a native solvent to a primary solvent which comprises:

adding a primary solvent to a first solution containing (a) a solute dissolved in a native solvent and (b) impurities which reduce the coalescence rate of at least one of said solvents, said primary solvent being added in amounts sufficient to form a single-phase mixture comprising said primary solvent, said native solvent end said solute;

adding a modifier to said single-phase solution in the presence of said impurities while said solution is subject to not more than gentle mixing, said modifier being miscible with either the primary solvent or the native solvent and serving to reduce the miscibility of the primary solvent with the native solvent so as to form an immiscible mixture which coalesces near instantaneously, to form two phases, one phase being rich in the native solvent end the second phase being rich in the primary solvent and solute; and thereafter separating said solute from the primary solvent-rich phase.

2. The extraction process of claim 1 wherein the first solution contains components which are barriers to extraction and the primary solvent is capable of penetrating such components so as to increase the amount of solute dissolved in the single-phase mixture.

3. The extraction process of claim 2 wherein the first solution contains cells and the components which are barriers to extraction are cell boundaries.

4. The extraction process of claim 1 wherein said first solution is a fermentation broth.

5. The extraction process of claim 1 wherein the native solvent is water.

6. The extraction process of claim 1 wherein the primary solvent is an organic solvent and wherein the modifier is an organic solvent.

7. The extraction process of claim 1 wherein the primary solvent is an organic solvent and a modifier is used, said modifier being an inorganic salt.

8. The extraction process of claim 1 wherein the process is carried out at a substantially constant temperature.

9. The extraction process of claim 8 wherein the substantially constant temperature is room temperature.

10. A liquid-liquid extraction process wherein a solute is transferred at a high mass transfer riots from water to a primary solvent which comprises:

adding a primary solvent to a fermentation broth containing (a) a solute dissolved in water and (b) impurities which reduce the coalescence rate of the water, the primary solvent, or both, said primary solvent being added in an amount sufficient to form a single-phase mixture;

adding a modifier to said single-phase solution in the presence of said impurities while said solution is subject to not more than gentle mixing, said modifier being miscible with the primary solvent or the native solvent and serving to reduce the miscibility of the primary solvent in water so as to form an immiscible mixture which coalesces, near instantaneously, into two phases, one phase being a water-rich phase and the second phase being rich in the solute and the primary solvent and modifier.

11. The extraction process of claim 10 wherein the primary solvent is acetonitrile and the modifier is methyl isobutyl ketone.

12. The extraction process of claim 10 wherein the solute is an antibiotic.

13. The extraction process of claim 12 wherein the antibiotic is efrotomycin.

14. The extraction process of claim 10 wherein the process is carried out substantially at room temperature.

15. The extraction process of claim 10 wherein the solute is separated from the solvent-rich phase.

* * * * *